(12) United States Patent
Miyauchi et al.

(10) Patent No.: US 10,168,343 B2
(45) Date of Patent: Jan. 1, 2019

(54) PROCESSING SYSTEM, CONTROL METHOD, OPERATION COMMAND GENERATING DEVICE AND COMPUTER PROGRAM

(71) Applicant: Kabushiki Kaisha Yaskawa Denki, Kitakyushu-shi (JP)

(72) Inventors: Kohei Miyauchi, Kitakyushu (JP); Makoto Umeno, Kitakyushu (JP); Jiro Muraoka, Kitakyushu (JP)

(73) Assignee: KABUSHIKI KAISHA YASKAWA DENKI, Kitakyushu-shi (JP)

( * ) Notice: Subject to any disclaimer, the term of this patent is extended or adjusted under 35 U.S.C. 154(b) by 255 days.

(21) Appl. No.: 15/216,208

(22) Filed: Jul. 21, 2016

(65) Prior Publication Data

US 2017/0023598 A1    Jan. 26, 2017

(30) Foreign Application Priority Data

Jul. 24, 2015   (JP) .................................. 2015-146599

(51) Int. Cl.
*G01N 35/00*   (2006.01)
*B01L 3/02*    (2006.01)
(Continued)

(52) U.S. Cl.
CPC ...... *G01N 35/00584* (2013.01); *B25J 9/1612* (2013.01); *B25J 9/1679* (2013.01);
(Continued)

(58) Field of Classification Search
None
See application file for complete search history.

(56) References Cited

U.S. PATENT DOCUMENTS

| 4,399,711 A * | 8/1983 | Klein | B01L 3/0217 |
| | | | 73/864.16 |
| 2005/0118069 A1* | 6/2005 | Solotareff | B01L 3/0217 |
| | | | 422/400 |
| 2013/0280143 A1* | 10/2013 | Zucchelli | B25J 9/1697 |
| | | | 422/501 |

FOREIGN PATENT DOCUMENTS

| JP | 10-323571 A | 12/1998 |
| JP | 2013-543984 A | 12/2013 |

OTHER PUBLICATIONS

Office Action dated Jan. 16, 2018 in Japanese Patent Application No. 2015-146599 (with unedited computer generated English translation), 7 pages.

* cited by examiner

*Primary Examiner* — Kathryn Wright
(74) *Attorney, Agent, or Firm* — Oblon, McClelland, Maier & Neustadt, L.L.P.

(57) ABSTRACT

A processing system for processing experiment of biochemistry, biology and/or biotechnology includes a manual pipette which includes a piston and suctions and discharges liquid when the piston of the manual pipette is moved by external drive force, an automatic pipette which includes a piston and a built-in actuator and suctions and discharges liquid when the piston of the automatic pipette is moved by the actuator, a robot including a robotic arm which selects and grasps the manual or automatic pipette based on an operation command, and a robotic arm control device including circuitry which controls the robot such that the robotic arm selects and grasps the manual or automatic pipette based on the operation command. The operation command includes a collection of jobs that controls processes for processing a processing target in an experiment of (Continued)

biochemistry, biology and/or biotechnology and a container containing the processing target in a processing order.

10 Claims, 10 Drawing Sheets

(51) Int. Cl.
*B25J 9/16* (2006.01)
*G01N 35/10* (2006.01)
(52) U.S. Cl.
CPC ..... *G01N 35/0099* (2013.01); *G01N 35/1009* (2013.01); *B01L 3/0217* (2013.01)

PROCESSING SYSTEM, CONTROL METHOD, OPERATION COMMAND GENERATING DEVICE AND COMPUTER PROGRAM

CROSS-REFERENCE TO RELATED APPLICATIONS

The present application is based upon and claims the benefit of priority to Japanese Patent Application No. 2015-146599, filed Jul. 24, 2015, the entire contents of which are incorporated herein by reference.

BACKGROUND OF THE INVENTION

Field of the Invention

The present invention relates to a processing system, a control method, an operation command generating device and a computer program.

Description of Background Art

In fields of biochemistry, biology and bioengineering, operations such as a series of tests, culture and amplification that are performed with respect to a processing target (hereinafter, these operations are collectively referred to as an "experiment") may include operations of sucking or discharging a liquid using a pipette.

SUMMARY OF THE INVENTION

According to one aspect of the present invention, a processing system for processing an experiment of biochemistry, biology or biotechnology includes a manual pipette which includes a piston and suctions and discharges a liquid when the piston of the manual pipette is moved by an external drive force, an automatic pipette which includes a piston and a built-in actuator and suctions and discharges a liquid when the piston of the automatic pipette is moved by the built-in actuator, a robot including a robotic arm which selects and grasps the manual pipette or the automatic pipette based on an operation command, and a robotic arm control device including circuitry which controls the robot such that the robotic arm selects and grasps the manual pipette or the automatic pipette based on the operation command. The operation command includes a collection of jobs that controls processes for processing a processing target in an experiment of biochemistry, biology or biotechnology and/or a container containing the processing target in a processing order.

According to another aspect of the present invention, a method for controlling a processing system which processes an experiment of biochemistry, biology or biotechnology includes generating an operation command based on process symbols which represent processes for a processing target in an experiment of biochemistry, biology or biotechnology and/or a container containing the processing target in a processing order, selecting which one of a manual pipette and an automatic pipette is to be used in a process based on the operation command, and controlling a robot including a robotic arm such that the robotic arm grasps the manual pipette or the automatic pipette selected based on the operation command. The generating of the operation command includes generating a first operation command when the manual pipette is determined to be used, and generating a second operation command when the automatic pipette is determined to be used, the controlling of the robot includes controlling the robotic arm based on the first operation command such that the robotic arm grasps the manual pipette and controlling the robotic arm based on the second operation command such that the robotic arm grasps the automatic pipette, the processing system includes the manual pipette which includes a piston and suctions and discharges a liquid when the piston of the manual pipette is moved by an external drive force, the automatic pipette which includes a piston and a built-in actuator and suctions and discharges a liquid when the piston of the automatic pipette is moved by the built-in actuator, the robot includes the robotic arm which selects and grasps the manual pipette or the automatic pipette based on the operation command, and a robotic arm control device including circuitry which controls the robot such that the robotic arm selects and grasps the manual pipette or the automatic pipette based on the operation command, and the operation command includes a collection of jobs that control the processes for processing the processing target and/or the container in the processing order.

According to yet another aspect of the present invention, an operation command generating device includes circuitry which generates an operation command which controls a robot based on process symbols which represent processes for a processing target in an experiment of biochemistry, biology or biotechnology and/or a container containing the processing target in a processing order. The circuitry of the operation command generating device determines which one of a manual pipette and an automatic pipette is to be used based on the process symbols, generates a first operation command when the manual pipette is determined to be used, and generates a second operation command when the automatic pipette is determined to be used, the manual pipette includes a piston and suctions and discharges a liquid when the piston of the manual pipette is moved by an external drive force, the automatic pipette includes a piston and a built-in actuator and suctions and discharges a liquid when the piston of the automatic pipette is moved by the built-in actuator, and the robot selects and grasp the manual pipette and/or the automatic pipette based on the operation command.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
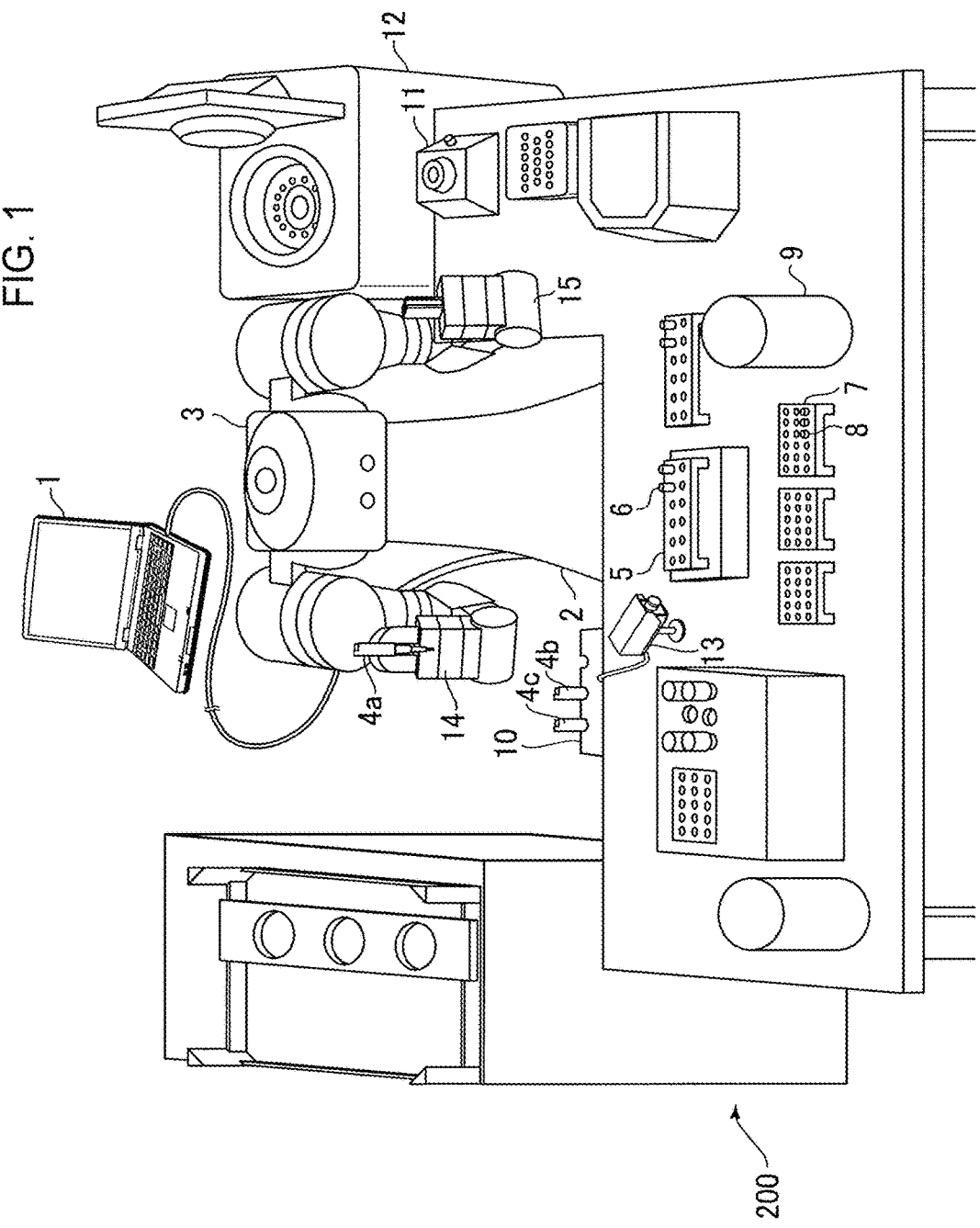
FIG. 1 is a schematic diagram illustrating a physical structure of a processing system according to an embodiment of the present invention.

The embodiments will now be described with reference to the accompanying drawings, wherein like reference numerals designate corresponding or identical elements throughout the various drawings.

FIG. 1 is a schematic diagram illustrating a physical structure of a processing system 200 according to an embodiment of the present invention. The processing system 200 includes an operation command generating device 1 that generates an operation command based on multiple process symbols that each represent a process with respect to a processing target or a process with respect to a container containing a processing target, a processing order having been determined for each of the multiple process symbols. Here, the multiple process symbols are described in a protocol chart that illustrates a protocol, and are symbols that visually express content of the protocol. The operation command generating device 1 may be a dedicated device. However, here, the operation command generating device 1 is implemented using a common computer. That is, in a commercially available computer, by executing a computer program that allows the computer to operate as the operation command generating device 1, such a computer is used as the operation command generating device 1. Such a computer program is generally provided in a form of application software, and is used by being installed on the computer. The application software may be provided by being recorded on a CD-ROM, a DVD-ROM, or other suitable computer readable information recording media, and further may also be provided via various information communication networks such as the Internet, or, may be implemented by so-called cloud computing in which the function of the operation command generating device 1 is provided by a remote server via an information communication network.

The processing system 200 includes a robotic arm control device 2 that controls at least a robotic arm based on an operation command that is generated by the operation command generating device 1. In the present embodiment, the processing system 200 includes a first robotic arm 14 that selectively grasps a first manual pipette (4a), a second manual pipette (4b) or an automatic pipette (4c). Here, the first manual pipette (4a) and the second manual pipette (4b) pipettes that each perform suction and discharge of a liquid when a piston is moved by an external drive force, and have mutually different capacities. The automatic pipette (4c) is a pipette that performs suction and discharge of a liquid when a piston is moved by a built-in actuator. Further, the processing system 200 includes a second robotic arm 15 that moves the piston of the first manual pipette (4a) or the second manual pipette (4b) that is grasped by the first robotic arm 14. The robotic arm control device 2 according to the present embodiment is integrally provided with a robot 3. However, the robotic arm control device 2 may also be separately provided from the robot 3.

According to the processing system 200 of the present embodiment, both the first manual pipette (4a) and the second manual pipette (4b), which allow operation of the piston to be arbitrarily adjusted, and the automatic pipette (4c), which allows a suction amount and a discharge amount of a liquid to be electronically adjusted, can be used. Therefore, selection of a pipette in accordance with characteristics becomes possible and processes that can be handled can be increased. As will be described in detail later, when a speed of suction or discharge is specified, a manual pipette is used for a case or the like where a position of a pipette is predicted and controlled so as to follow a liquid level change. Further, in cases such as where a liquid contained in a pipette is specified to be discharged into multiple containers, where a position of a pipette is feedback-controlled so as to follow a change in a position of a liquid level that is photographed by a camera 13, or where a container and a pipette are tilted, the automatic pipette is used. Here, the camera 13 included in the processing system 200 continuously photographs a position of a liquid level of a liquid contained in a microtube 6.

The robot 3 is a multi joint robot, and performs a process with respect to a processing target using the first robotic arm 14 and the second robotic arm 15. The robot 3 can operate laboratory instruments (illustrated or not illustrated in the drawings). For example, the robot 3 can use the first robotic arm 14 to grasp the first manual pipette (4a), the second manual pipette (4b) and the automatic pipette (4c), which are accommodated in a pipette rack 10, and operate. Further, the robot 3 can move various containers (illustrated or not illustrated in the drawings), For example, the robot 3 can use the second robotic arm 15 to grasp a microtube 6, which is stored in a tube rack 5, and move the microtube 6 from the tube rack 5 to a vortex mixer 11, a centrifugal separator 12, or the like. In the present embodiment, when the robot 3 uses the first robotic arm 14 to grasp the pipette 4 to suck or inject a chemical solution, the robot 3 performs operation by attaching a chip 8, which is prepared in a chip rack 7, to a front end of the pipette 4. The chip 8, in principle, is disposable. A used chip 8 is discarded into a dust box 9.

In the example illustrated in FIG. 1, the first manual pipette (4a), the second manual pipette (4b) and the automatic pipette (4c) are prepared in the pipette rack 10, and among the pipettes, the first manual pipette (4a) is grasped by the robot 3 using the first robotic arm 14. Further, in the processing system 200 according to the present embodiment, the vortex mixer 11, the centrifugal separator 12 and the like are included. However, these are examples of instruments that are used in performing an experiment. In addition to or in place of these instruments, other instruments may also be included. For example, in the processing system 200, a rack that stores Petri dishes, a magnet rack, and the like may also be included. Further, the robot 3 according to the present embodiment is a two-arm robot. The robot 3 is provided with the first robotic arm 14 and the second robotic arm 15. However, it is not necessarily required that at least one robotic arm of the processing system 200 is provided to one robot. For example, it is also possible that multiple robotic arms are separately and independently provided and are controlled by the robotic arm control device 2 to operate in cooperation.

As robotic arms included in a processing system, it is possible to provide a dedicated robotic arm that handles a manual pipette and a dedicated robotic arm that handles an automatic pipette. However, it is possible that an overall operation efficiency of the processing system is reduced because it may occur that an operation rate of one of the dedicated robotic arms is high and an operation rate of another dedicated robotic arm is low, or a waiting time may occur to one of the dedicated robotic arms. In this regard, according to the processing system 200 of the present embodiment, without providing a dedicated arm for each of the pipettes, the processing system 200 with a high operation efficiency can be obtained in which the manual pipettes and the automatic pipette can be selectively used, and operation rates of the robotic arms included in the processing system 200 are kept high.

Figure 2:
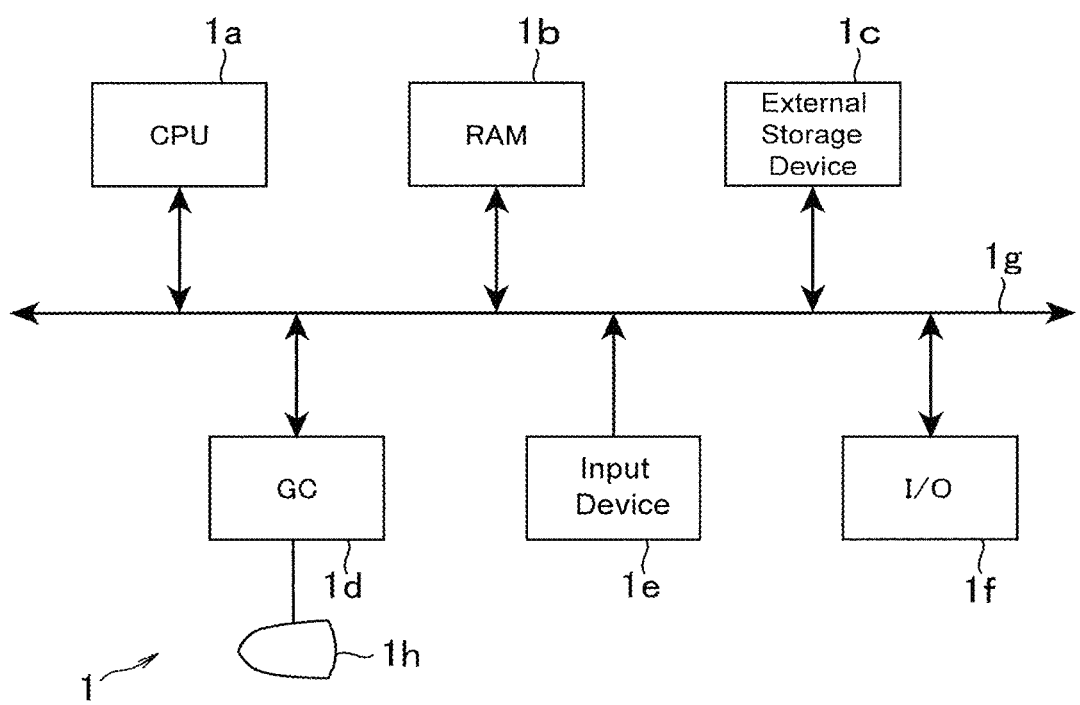
FIG. 2 is a structural block diagram illustrating a physical structure of an operation command generating device according to the embodiment of the present invention.

FIG. 2 is a block diagram illustrating a physical structure of the operation command generating device 1 according to the embodiment of the present invention. The structure illustrated in FIG. 2 illustrates the common computer that is used as the operation command generating device 1, in which a CPU (Central Processing Unit) (1a), a RAM (Random Access Memory) (1b), an external storage device (1c), a GC (Graphics Controller) (1d), an input device (1e) and an I/O (Input/Output) (1f) are connected by a data bus (1g) so as to be able to exchange electrical signals between each other. Here, the external storage device (1c) is a device such as a HDD (Hard Disk Drive) or a SSD (Solid State Drive) that can record static information. Further, a signal from the GC (1d) is output to a monitor (1h) such as a flat panel display, which allows a user to visually recognize an image, and is displayed as an image. The input device (1e) is a device such as a keyboard or a mouse for a user to input information. The I/O (1f) is an interface for the operation command generating device 1 to exchange information with an external device.

Figure 3:
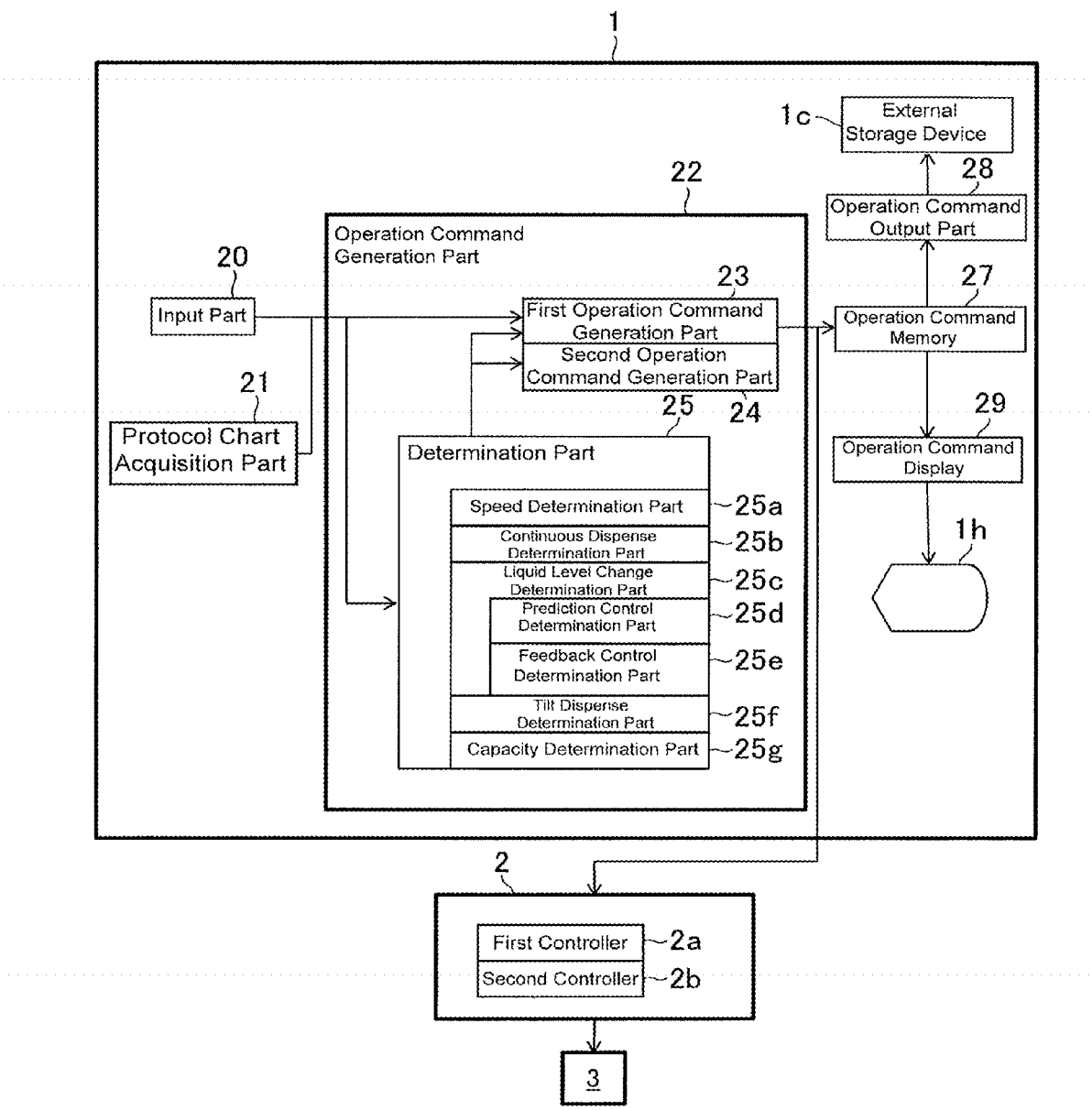
FIG. 3 is a functional block diagram of the operation command generating device, a robotic arm control device and a robot according to the embodiment of the present invention.

FIG. 3 is a functional block diagram of the operation command generating device 1, the robotic arm control device 2 and the robot 3 according to the embodiment of the present invention. The functional blocks illustrated here are focused on functions of the operation command generating device 1 and the like. Physical structures that are in one-to-one correspondence to the functional blocks do not necessarily exist. Some of the functional blocks may be implemented by executing a specific software program by an information processing device such the CPU (1a) of the operation command generating device 1; and some of the functional blocks may be implemented by allocating a specific storage area in an information storage device such as the RAM (1b) of the operation command generating device 1.

The operation command generating device 1 has an input part 20 that receives various inputs from a user, and a protocol chart acquisition part 21 that acquires a protocol chart that illustrates a protocol. Further, the operation command generating device 1 has an operation command generation part 22 that generates an operation command based on an input received by the input part 20 and a protocol chart acquired by the protocol chart acquisition part 21. Further, the operation command generating device 1 has an operation command memory 27 that stores electronic data during operation command generation or electronic data of a generated operation command, an operation command output part 28 that outputs a generated operation command as an electronic file in a form readable by the robot, and an operation command display 29 that forms the electronic data of the operation command stored in the operation command memory 27 and displays the electronic data on the monitor (1h).

The input part 20 is usually formed by the input device (1e) illustrated in FIG. 2. However, when the operation command generating device 1 is an application server used in cloud computing, the I/O (1f) through which operation information of a user on a remote terminal is input corresponds to the input part 20.

The operation command generation part 22 includes various functional blocks for generating an operation command. As will described in detail later in accordance with when procedures for generating an operation command are described, the operation command generation part 22 according to the present embodiment includes a first operation command generation part 23 that generates a first operation command that causes a robotic arm to grasp a manual pipette, and a second operation command generation part 24 that generates a second operation command that causes a robotic arm to grasp the automatic pipette. Further, the operation command generation part 22 includes a determination part 25 that determines whether to use a manual pipette or the automatic pipette based on a process symbol that is included in a protocol chart. In a case where the process symbol is associated with a specification of a particular mode of suction and discharge, the determination part 25 determines whether to use a manual pipette or the automatic pipette based on the specification of the mode. When the determination part 25 has determined that a manual pipette is used, the first operation command generation part 23 generates a first operation command. Further, when the determination part 25 has determined that the automatic pipette is used, the second operation command generation part 24 generates a second operation command.

In the present specification, an operation command is a single job or a collection of jobs in which multiple jobs are combined, and refers to a command that specifies a process that is recognized as a single unit of operation with respect to a container in which a processing target is contained. The operation command is generated by converting symbols displayed in a protocol chart into jobs that are each a unit operation of the robot and integrating the converted jobs by adding an execution order to each job.

The determination part 25 includes a speed determination part (25a), a continuous dispense determination part (25b), a liquid level change determination part (25c), a tilt dispense determination part (25f) and a volume determination part (25g). Further, the liquid level change determination part (25c) includes a prediction control determination part (25d) and a feedback control determination part (25e).

When a specification of a mode that is included in a process symbol is a specification of a speed of suction or discharge, the speed determination part (25a) determines that a manual pipette is used. Further, when a specification of a mode is a specification to discharge a liquid contained in a pipette into multiple containers, the continuous dispense determination part (25b) determines that the automatic pipette is used. Further, when a specification of a mode is a follow specification for causing a manual pipette or the automatic pipette to move so as to follow a change in a position of a liquid level of a liquid contained in a container, the liquid level change determination part (25c) determines whether to use a manual pipette or the automatic pipette. When the specification of the mode is a follow specification, the prediction control determination part (25d) determines that a manual pipette is used. Further, when the specification of the mode is a follow specification and is a specification involving photographing a change in a position of a liquid level of a liquid, the feedback control determination part (25e) determines that the automatic pipette is used. In a case of a specification for sucking a liquid contained in a container or discharging a liquid into a container by tilting the container and a pipette, the tilt dispense determination part (25*f*) determines that the automatic pipette is used. When a process symbol does not include a specification of a particular mode of suction and discharge, based on at least a volume of suction and discharge, the volume determination part (25*g*) determines whether to use a manual pipette or the automatic pipette.

The robotic arm control device 2 includes a first controller (2*a*) and a second controller (2*b*). The first controller (2*a*) performs control in which the first robotic arm 14 is caused to grasp the first manual pipette (4*a*) or the second manual pipette (4*b*) based on a first operation command that is included in an operation command that is a collection of jobs that control the processing system 200. Further, the second controller (2*b*) performs control in which the first robotic arm 14 is caused to grasp the automatic pipette (4*c*) based on a second operation command that is included in the operation command.

According to the processing system 200 of the present embodiment, whether to use a manual pipette or the automatic pipette is controlled by the first controller (2*a*) and the second controller (2*b*) of the robotic arm control device 2, and a reproducible experiment is performed. Further, a selection of a pipette is determined in advance based on an operation command, so that it is possible to reduce uncertain factors caused by a difference between pipettes, and the reproducibility of the experiment can be improved.

Further, according to the processing system 200 of the present embodiment, whether to use a manual pipette or the automatic pipette is determined by the determination part 25 based on a protocol chart, so that it is possible to reduce uncertain factors caused by a difference between pipettes and a reproducible experiment can be performed. Further, based on the process symbols, a pipette to be used is determined, and uncertain factors of an experiment can be reduced. Further, an optimal pipette is selected for each process, and an experiment can be more accurately performed.

Figure 4:
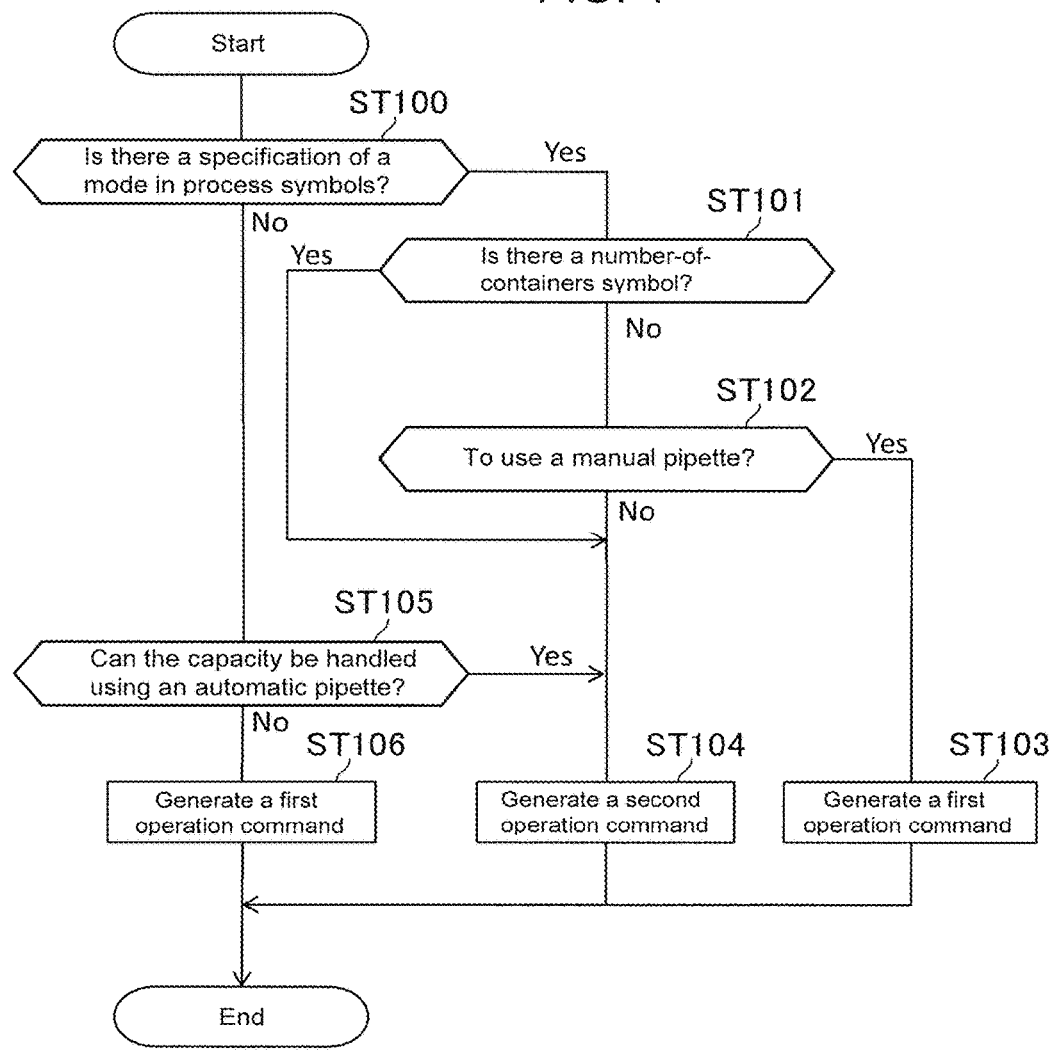
FIG. 4 is a flowchart illustrating a control method of the processing system according to the embodiment of the present invention.

FIG. 4 is a flowchart illustrating a control method of the processing system 200 according to the embodiment of the present invention. Control of the processing system 200 begins with a determination, by the determination part 25 of the operation command generating device 1, of whether or not a process symbol included in a protocol chart is associated with a specification of a particular mode of suction and discharge (ST100). Here, the particular mode of suction and discharge indicates a procedure in a case where a pipette process is performed. A specification of a mode may be, for example, a specification to suck only a supernatant liquid of a liquid contained in a microtube 6, or a specification to perform suction or discharge of a liquid without immersing a chip 8 in the liquid.

When a process symbol is associated with a specification of a mode, whether or not a number-of-containers symbol is included is determined, the number-of-containers symbol indicating that a same process is repeated for multiple containers (ST101). When the number-of-containers symbol is included, a second operation command is generated that causes the first robotic arm 14 to grasp the automatic pipette (4*c*) (ST104). When a number-of-containers symbol is not included, based on a process symbol and a specification of a mode, whether or not a manual pipette is used is determined (ST102). When it is determined that a manual pipette is sued, a first operation command is generated that causes the first robotic arm 14 to grasp either the first manual pipette (4*a*) or the second manual pipette (4*b*) (ST103). On the other hand, when it is determined that a manual pipette is not used, that is, when it is determined that the automatic pipette is used, a second operation command is generated that causes the first robotic arm 14 to grasp the automatic pipette (4*c*) (ST104).

When the process symbol does not include a specification of a particular mode of suction and discharge, it is determined whether or not a volume of a liquid to be handled using a pipette is a volume that can be handled using the automatic pipette (4*c*) (ST105). When the process symbol does not include a specification of a particular mode of suction and discharge, based on at least a volume of suction and discharge, the volume determination part (25*g*) according to the present embodiment determines whether to use a manual pipette or the automatic pipette. When the volume of the liquid is a volume that can be handled using the automatic pipette (4*c*), a second operation command is generated that causes the first robotic arm 14 to grasp the automatic pipette (4*c*) (ST104). On the other hand, when the volume of the liquid is a volume that cannot be handled using the automatic pipette (4*c*), a first operation command is generated that causes the first robotic arm 14 to grasp the first manual pipette (4*a*) or the second manual pipette (4*b*) (ST106). Here, a volume that cannot be handled using the automatic pipette (4*c*) is, for example, a volume of 1 μl or less, or a volume of 1 ml (1000 μl) or more. However, it is also possible to allow a user to set the thresholds for each specification of a pipette. A process symbol may also include an explicit selection of using either a manual pipette or the automatic pipette. In this case, the determination part 25 determines whether to use a manual pipette or the automatic pipette according to the explicit selection.

In the processing system 200 according to the present embodiment, the determination part 25 determines whether to use a manual pipette or the automatic pipette for each process, and thereby a more appropriate pipette can be selected and precision and efficiency of an experiment can be improved. Further, a protocol chart that is acquired by the operation command generating device 1 according to the present embodiment includes a specification of a particular mode of suction and discharge (specification of a procedure). The operation command generating device 1 according to the present embodiment selects an appropriate pipette according to a specified procedure and, by replicating various procedures, can improve precision and efficiency of an experiment.

Further, in the processing system 200 according to the present embodiment, due to the volume determination part (25*g*), even when a specification of suction or discharge of a volume that cannot be handled using the automatic pipette is included in a protocol chart, an experiment can be performed in a way as instructed by the protocol chart without generating any error.

Figure 5:
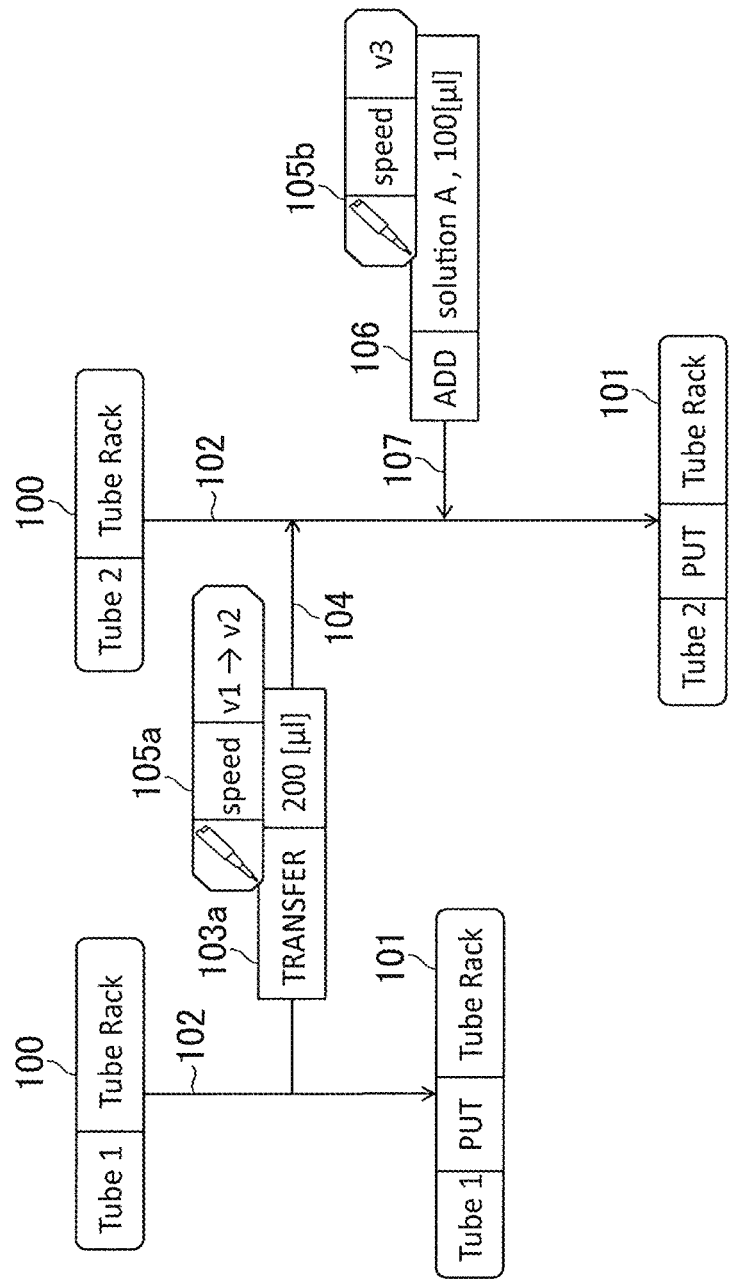
FIG. 5 illustrates an example of a first protocol chart that is acquired by the operation command generating device according to the embodiment of the present invention.

FIG. 5 illustrates an example of a first protocol chart that is acquired by the operation command generating device 1 according to the embodiment of the present invention. The example of the first protocol chart includes an initial symbol 100 that indicates a "Tube 1" (first microtube) that is accommodated in a "Tube Rack" (the tube rack 5), and an initial symbol 100 that indicates a "Tube 2" (second microtube) that is accommodated in the tube rack 5. The initial symbols 100 are respectively connected by order lines 102 to final symbols 101 that indicate returning the microtubes to the tube rack 5. Processing orders of multiple process symbols are determined by the order lines 102.

The example of the first protocol chart includes a transfer line 104 that extends from the order line 102 for the first microtube to the order line 102 for the second microtube.

The transfer line 104 is accompanied by a transfer symbol (103a) that is indicated as "TRANSFER." The transfer symbol (103a) is described as "200 µl," which indicates that 200 µl of a liquid contained in the first microtube is to be transferred to the second microtube. A speed change specification symbol (105a) is displayed overlapping with the transfer symbol (103a), and is associated with the transfer symbol (103a). The speed change specification symbol (105a) indicates a specification for causing a suction speed to change when the liquid contained in the first microtube is sucked by a pipette such that the suction begins at an initial speed of v1 µl/s and ends at a final speed of v2 Wis. Here, it is assumed that v1>v2, and the specification is to change the suction speed such that the suction speed monotonically decreases. When a speed that changes with time is specified by the speed change specification symbol (105a), the speed determination part (25a) determines that a manual pipette is used. In response to the determination, the first operation command generation part 23 generates a first operation command that causes the piston of the manual pipette to be moved by the second robotic arm 15 at a speed that changes with time corresponding to a specified speed. In this case, by grasping the first manual pipette (4a) or the second manual pipette (4b) using the first robotic arm 14 and pressing the piston using the second robotic arm 15, the robot 3 can move the piston of the manual pipette at a desired speed, and can suck the liquid in a way as specified by the speed change specification symbol (105a). Even in a case of a specification that causes a discharge speed to change with time, similar to the case of suction, by grasping the first manual pipette (4a) or the second manual pipette (4b) using the first robotic arm 14 and pressing the piston using the second robotic arm 15, a process as specified can be performed.

By allowing a speed at which a liquid is sucked to change with time, for example, when precipitates are accumulated at a bottom of the microtube 6, the suction speed can be slowed as a front end of a chip 8 comes close to the precipitates, and suction of the precipitates can be avoided. Therefore, diffusion of the precipitates and unintended suction of the precipitates are suppressed, and the precision of the experiment is improved.

The example of the first protocol chart includes an add line 107 that is illustrated as connecting to the order line 102 for the second microtube. An add symbol 106 is connected to the add line 107, and it is indicated that "100 µl" of a "Solution A" is to be added to the second microtube. In the case of the example of the first protocol chart, before the "Solution A" is added, a liquid is transferred from the first microtube to the second microtube. Therefore, the "Solution A" is added to the liquid that is transferred from the first microtube.

A speed specification symbol (105b) is displayed overlapping with the add symbol 107, and is associated with the add symbol 106. The speed specification symbol (105b) specifies that discharge of a liquid is performed at a speed of v3 µl/s. When the specification by the speed specification symbol (105b) is a specification of a speed of suction or discharge to which the automatic pipette (4c) does not correspond, the speed determination part (25a) determines that a manual pipette is used. In the case of the present example, when discharge by the automatic pipette (4c) at the speed of v3 µl/s cannot be performed, the speed determination part (25a) determines that a manual pipette is used. In this case, the first operation command generation part 23 generates a first operation command that causes the piston to be moved by the second robotic arm 15 at a speed corresponding to a specified speed. In this case, by grasping the first manual pipette (4a) or the second manual pipette (4b) using the first robotic arm 14 and pressing the piston using the second robotic arm 15, the robot 3 can move the piston of the manual pipette at a desired speed, and can discharge the liquid in a way as specified by the speed specification symbol (105b). Even in a case where a suction speed is specified, similar to the case of discharge, by grasping the first manual pipette (4a) or the second manual pipette (4b) using the first robotic arm 14 and pressing the piston using the second robotic arm 15, a process as specified can be performed.

When the speed determination part (25a) determines whether or not a speed of suction or discharge is that to which the automatic pipette (4c) does not correspond, it is also possible that a threshold of the speed is set in advance by a user. For example, when the speed of suction or discharge is a slow speed of a certain value or less, it may be determined that a manual pipette is used. According to the processing system 200 of the present embodiment, even in the case of relatively slow suction or discharge that the automatic pipette cannot handle, by adjusting the pressing speed of the robotic arm with which the piston of the manual pipette is pressed, a process can be performed in a way as specified. Therefore, a chemical solution or the like that is sensitive to an impact can be handled without causing a change in characteristics thereof, and an experiment can be more reliably performed.

Figure 6:
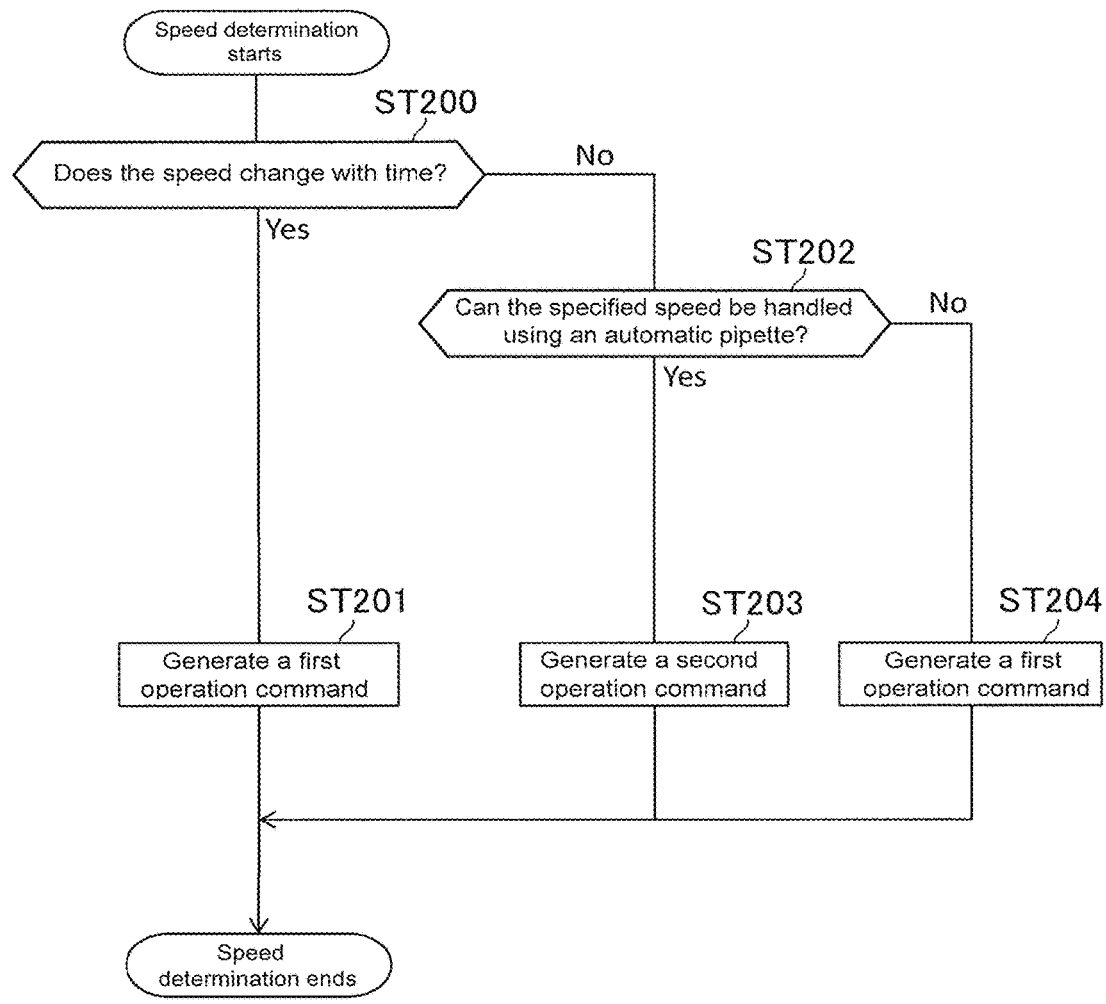
FIG. 6 is a flowchart illustrating determination performed by a speed determination part of the operation command generating device according to the embodiment of the present invention.

FIG. 6 is a flowchart illustrating a determination performed by the speed determination part (25a) of the operation command generating device 1 according to the embodiment of the present invention. When a process symbol displayed in a protocol chart includes a specification of a particular mode of suction or discharge and the specification of the mode is a specification of a speed of suction or discharge, the speed determination part (25a) determines whether or not the specified speed changes with time (ST200). When the specified speed changes with time, the speed determination part (25a) determines that a manual pipette is used. In response to the determination, the first operation command generation part 23 generates a first operation command that causes the first robotic arm 14 to grasp the first manual pipette (4a) or the second manual pipette (4b) and the second robotic arm 15 to move the piston at a speed corresponding to the specified speed (ST201).

On the other hand, when the specified speed does not change with time, whether or not the specified speed is a speed that can be handled using the automatic pipette (4c) is determined (ST202). When the specified speed is a speed that can be handled using the automatic pipette (4c), a second operation command is generated that instructs the first robotic arm 14 to grasp the automatic pipette (4c) and the piston to be moved at a speed corresponding to the specified speed (ST203). The instruction to move the piston of the automatic pipette (4c) can be performed by wireless communication between the robotic arm control device 2 or the like and the automatic pipette (4c). When the specified speed is a speed that cannot be handled using the automatic pipette (4c), a first operation command is generated that causes the first robotic arm 14 to grasp the first manual pipette (4a) or the second manual pipette (4b) and the second robotic arm 15 to move the piston at a speed corresponding to the specified speed (ST204).

Figure 7:
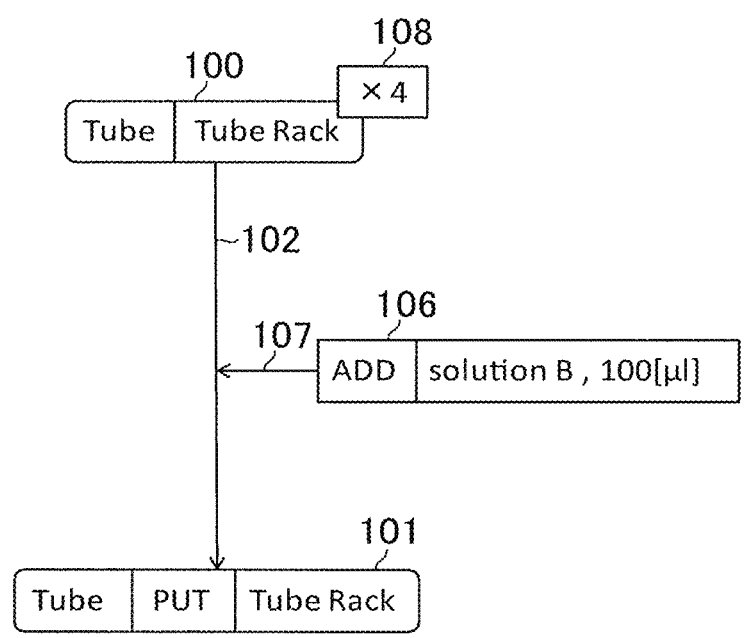
FIG. 7 illustrates an example of a second protocol chart that is acquired by the operation command generating device according to the embodiment of the present invention.

FIG. 7 illustrates an example of a second protocol chart that is acquired by the operation command generating device 1 according to the embodiment of the present invention. The example of the second protocol chart includes an initial symbol 100 that indicates preparing a microtube 6 that is indicated as "Tube" from a "Tube Rack" (the tube rack 5) to a work area, an add symbol 106 that indicates adding "100 µl" of a "SolutionB" to the microtube 6, and a final symbol 101 that indicates returning the microtube 6 to the tube rack 5. Here, a number-of-containers symbol 108 that is indicated as "×4" is positioned so as to overlap with the "initial symbol 100. The number-of-containers symbol 108 indicates that the process that is performed with respect to the container indicated by the associated initial symbol 100 is repeated with respect to multiple containers of the same kind. In the case of the example of the second protocol chart, the number-of-containers symbol 108 indicates that a process in which "100 µl" of a "Solution B" is added to the microtube 6 is repeated with respect to four containers.

When the initial symbol 100, which is one kind of a process symbol, is associated with a specification to discharge a liquid contained in a pipette into multiple containers, the continuous dispense determination part (25*b*) determines that the automatic pipette is used. As in the example of the second protocol chart, the number-of-containers symbol 108 is associated with the initial symbol 100. When it is indicated by the add symbol 106 that a liquid contained in a pipette is to be discharged into a container, it is associated with a specification to discharge the liquid contained in the pipette into multiple containers, and the continuous dispense determination part (25*b*) determines that the automatic pipette (4*c*) is used. In response to the determination, the second operation command generation part 25 generates second operation command that causes the first robotic arm 14 to operate and a liquid that is sucked into the automatic pipette (4*c*) to be sequentially discharged into multiple containers that are prepared in the work area in the number indicated by the number-of-containers symbol 108. The liquid that is to be discharged into the multiple containers may be contained in the automatic pipette (4*c*) by one suction.

A manual pipette in general is used such that, when a liquid contained therein is discharged, in principle, the liquid contained therein is completely discharged. It is also possible that the liquid is divided and discharged by stopping the piston in the middle of the process, but this may result in that a sufficient precision cannot be obtained. On the other hand, the automatic pipette has a feature that the piston is moved by the built-in actuator so that the piston can be stopped at any position and a liquid contained therein can be divided and discharged with high precision. The processing system 200 according to the present embodiment utilizes such a feature of the automatic pipette, and eliminates the need of sucking a liquid in each discharge when the same kind of liquid is discharged into multiple containers. As a result, dispensing can be continuously performed, and an experiment can be more efficiently performed and can be more quickly completed.

Figure 8:
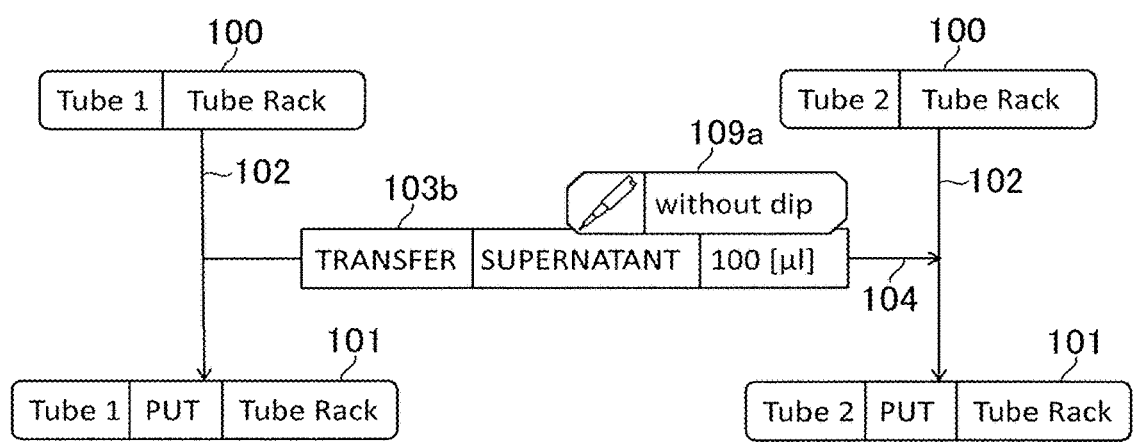
FIG. 8 illustrates an example of a third protocol chart that is acquired by the operation command generating device according to the embodiment of the present invention.

FIG. 8 illustrates an example of a third protocol chart that is acquired by the operation command generating device 1 according to the embodiment of the present invention. The example of the third protocol chart includes a supernatant transfer symbol (103*b*) that indicates transferring a supernatant liquid of a liquid contained in a first microtube indicated as a "Tube 1" to a second microtube indicated as a "Tube 2." The supernatant transfer symbol (103*b*), by an indication of "SUPERNATANT," indicates a specification for sucking a supernatant liquid. By sucking a supernatant liquid, for example, only a supernatant liquid of a liquid that has been separated into two layers by the centrifugal separator 12 can be transferred to another container.

A wet avoidance symbol (109*a*) that is indicated as "without dip" is displayed overlapping with the supernatant transfer symbol (103*b*), and is associated with the supernatant transfer symbol (103*b*). The wet avoidance symbol (109*a*) is a specification of a mode of suction and discharge associated with the supernatant transfer symbol (103*b*), which is one kind of a process symbol, and is a follow specification for causing a manual pipette or the automatic pipette to move so as to follow a change in a position of a liquid level of a liquid contained in a container. In the case where a liquid is sucked or discharged by a pipette, when a chip 8 that is attached to a front end of the pipette is immersed in a liquid that is contained in a container, the chip 8 is wet, and a volume of a liquid that is discharged into the container or a volume of a liquid that is sucked by the pipette may be smaller than an intended volume. In the processing system 200 according to the present embodiment, when there is a specification by the wet avoidance symbol (109*a*), suction is performed by causing a pipette to follow a liquid level of a liquid contained in a container such that a state is maintained in which a front end of a chip 8 is in contact with the liquid level. As a result, the chip 8 can be prevented from becoming wet, a liquid attached to the chip 8 can be reduced, a volume of a liquid can be more precisely controlled, and an experiment can be performed with good precision. Also when discharge is performed, a pipette may be moved to follow a liquid level such that a state is maintained in which a front end of a chip 8 is in contact with the liquid level. Also when discharge is performed, by moving a pipette such that a front end of a chip 8 follows a liquid level, even when there is a situation such as where a liquid is sensitive to an impact and dropping the liquid is unfavorable, the liquid can be discharged without causing a change in characteristics of the liquid, and an experiment can be more reliably performed.

When a specification of a mode of suction and discharge associated with a process symbol is a follow specification, the prediction control determination part (25*d*) that is included in the liquid level change determination part (25*c*) according to the present embodiment determines that a manual pipette is used. In response to the determination, the first operation command generation part 23 generates a first operation command that causes control of the robotic arms to be performed in which a change in a position of a liquid level of a liquid is predicted. When the example of the third protocol chart is acquired, the first operation command generation part 23 according to the present embodiment generates a first operation command that causes the first robotic arm 14 to grasp the first manual pipette (4*a*) or the second manual pipette (4*b*), and causes the second robotic arm 15 to move the piston while the first robotic arm 14 is caused to be lowered to the microtube 6 at a predetermined speed. Here, the speed at which the first robotic arm 14 is lowered to the microtube 6 is synchronized with the speed at which the liquid level of the liquid contained in the microtube 6 drops due to the suction of the liquid by the manual pipette. In operation command generating device 1 according to the present embodiment, the speed at which the first robotic arm 14 is lowered to the microtube 6 is calculated in advance from a diameter of the microtube 6, a volume of the liquid contained in the microtube 6 and the speed of the suction by the manual pipette.

According to the processing system 200 of the present embodiment, when there is a specification to avoid wetting of the chip 8, liquid level following control of the pipette is performed based on a predetermined speed, and the liquid is sucked or discharged with high precision. As a result, a liquid attached to the chip 8 is reduced, and the precision of the experiment is improved, and thus, reproducibility of the experiment is improved.

Figure 9:
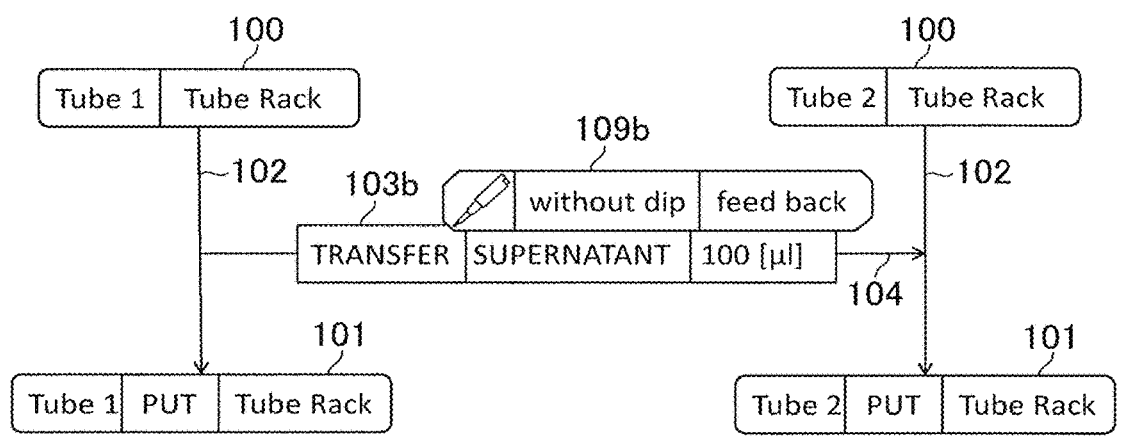
FIG. 9 illustrates an example of a fourth protocol chart that is acquired by the operation command generating device according to the embodiment of the present invention.

FIG. 9 illustrates an example of a fourth protocol chart that is acquired by the operation command generating device 1 according to the embodiment of the present invention. The example of the fourth protocol chart includes a feedback-based wet avoidance symbol (109*b*) that is displayed overlapping with the supernatant transfer symbol (103*b*) and is associated with the supernatant transfer symbol (103*b*). Other symbols of the example of the fourth protocol chart are the same as those in the example of the third protocol chart. The feedback-based wet avoidance symbol (109*b*) is indicated as "feedback" and indicates performing liquid level following by real-time feedback control using photographing by the camera 13. The camera 13 is a device that photographs a change in a position of a liquid level of a liquid contained in a container such as the microtube 6.

When a specification of a mode of suction and discharge associated with a process symbol is a follow specification and is a specification involving photographing a change in a position of a liquid level of a liquid contained in a container, the feedback control determination part (25*e*) that is included in the liquid level change determination part (25*c*) according to the present embodiment determines that the automatic pipette is used. In response to the determination, the second operation command generation part 24 generates the second operation command that causes control of the robotic arms to be performed in which a change in a position of a liquid level of a liquid is photographed. When the example of the fourth protocol chart is acquired, the second operation command generation part 24 according to the present embodiment generates a second operation command that causes the first robotic arm 14 to grasps the automatic pipette (4*c*), causes the automatic pipette (4*c*) to perform suction or discharge, causes the camera 13 to photograph a change in a position of a liquid level of a liquid contained in a microtube 6, and causes the first robotic arm 14 to move such that a state is maintained in which a front end of a chip 8 that is attached to the automatic pipette (4*c*) is in contact with the liquid level of the liquid contained in the microtube 6. Here, a speed at which the first robotic arm 14 is lowered to the microtube 6 is feedback controlled so as to be synchronized with the change in the position of the liquid level that is photographed by the camera 13. When such control is performed in suction or discharge using a manual pipette, the first robotic arm 14 is moved such that the manual pipette follows the liquid level while the piston of the manual pipette is pressed by the second robotic arm 15, and the control becomes complicated. However, when it is possible to use a single robotic arm to grasp a manual pipette and press the piston, a feedback-based wet avoidance operation may also be performed using the manual pipette.

According to the processing system 200 of the present embodiment, even when a kind of a container and a kind of a pipette are not certain and when a speed at which a position of a liquid level changes and a suction speed cannot be determined in advance, feedback control is performed by photographing in real time the change in the position of the liquid level using the camera 13. Therefore, a wet avoidance operation can be reliably performed, a liquid attached to the chip 8 can be reduced, and the precision of an experiment can be improved, and thus the reproducibility of the experiment can be improved.

Figure 10:
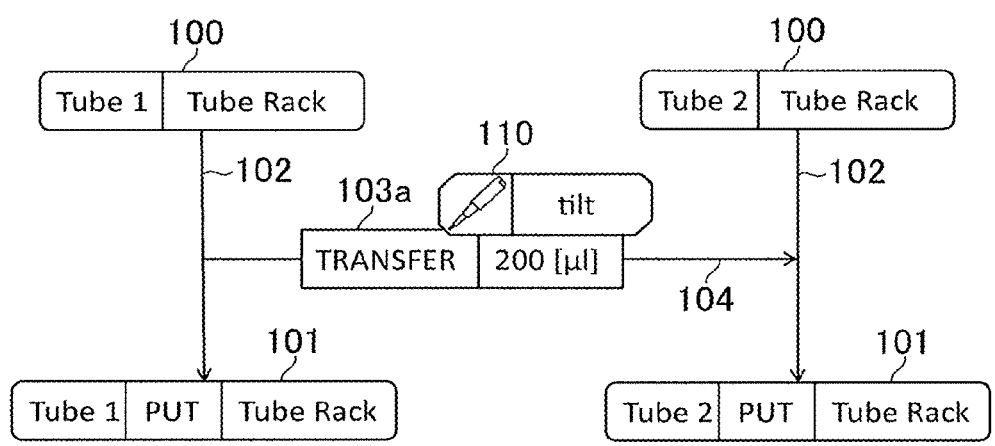
FIG. 10 illustrates an example of a fifth protocol chart that is acquired by the operation command generating device according to the embodiment of the present invention.

FIG. 10 illustrates an example of a fifth protocol chart that is acquired by the operation command generating device 1 according to the embodiment of the present invention. The example of the fifth protocol chart includes a transfer symbol (103*a*) that indicates transferring "200 µl" of a liquid contained in a first microtube that is indicated as "Tube 1" to a second microtube that is indicated as "Tube 2." A tilt symbol 110 that is indicated as "tilt" is displayed overlapping with the transfer symbol (103*a*), and is associated with the transfer symbol (103*a*). The tilt symbol 110 is a specification of a mode of suction and discharge associated with the transfer symbol (103*a*), which is one kind of a process symbol, and is a specification for sucking a liquid contained in a container or a specification for discharging a liquid contained in a container by tilting the container and a pipette. By tilting a container and a pipette and sucking a liquid contained in the container, it is possible to more reliably suck only a supernatant of the liquid. Further, by tilting a container and a pipette and discharging a liquid into the container, the liquid can be contained in the container without causing an impact to the liquid.

In the case of a specification for sucking a liquid contained in a container or discharging a liquid into a container by tilting the container and a pipette, the tilt dispense determination part (25*f*) according to the present embodiment determines that the automatic pipette is used. In response to the determination, the second operation command generation part 24 generates a second operation command that causes the second robotic arm 15 to grasp a container and causes a liquid contained in the container to be sucked or a liquid to be discharged into the container by tilting the container and the automatic pipette. When the example of the fifth protocol chart is acquired, the second operation command generation part 24 according to the present embodiment generates a second operation command that causes the first robotic arm 14 to grasp the automatic pipette (4*c*), causes the second robotic arm 15 to grasp the microtube 6, and causes the automatic pipette (4*c*) to perform suction or discharge by tilting the automatic pipette (4*c*) and the microtube 6. Here, an inclination angle of the automatic pipette (4*c*) that is grasped by the first robotic arm 14 and an inclination angle of the microtube 6 that is grasped by the second robotic arm 15 are about the same and may be determined in advance by a user. Further, the inclination angles may also be determined according to a volume of a liquid contained in a container. For example, the inclination angle may be increased when the volume of the liquid contained in the container is relatively small, and may be decreased when the volume of the liquid contained in the container is relatively large.

According to the processing system 200 of the present embodiment, by using the first robotic arm 14 to grasp the automatic pipette (4*c*) and using the second robotic arm 15 to grasp the microtube 6, the pipette and the container can be arbitrarily tilted, and processing can be performed at various angles.

In a case where multiple specifications of modes (specifications of procedures) described above are mixed in one protocol chart, when the determination part 25 determines whether to use a manual pipette or the automatic pipette, the determination may be performed by providing an order of priority for each specification of a mode, or the determination may be performed by limiting switching between pipettes within a predetermined period of time in order to avoid frequent switching between the pipettes, or the determination may also be performed using other methods.

As pipettes used in experiments in the fields of biochemistry, biology and biotechnology, a manual pipette and an electronic pipette have mutually different characteristics and handling methods. Further, a pipette may be operated using a robotic arm. However, it is designed to operate one pipette, that is, either only the manual pipette or only the electronic pipette is handled.

When dedicated robotic arms are respectively provided for the manual pipette and the electronic pipette, the number of parts of the entire processing system is increased, which may cause an increase in cost. Further, the dedicated robotic arms are not necessarily always in operation, which may cause a decrease in an overall operation rate of the processing system and an increase in operation cost.

A processing system according to an embodiment of the present invention, a control method according to an embodiment of the present invention, an operation command generating device according to an embodiment of the present invention and a computer program according to an embodiment of the present invention allow both a manual pipette and an electronic pipette to be efficiently operated using a general-purpose robotic arm, and another embodiment of the present invention is a new and original processing system.

A pipette that is used in an experiment can be arbitrarily selected. However, characteristics of a pipette that is used in an experiment may significantly affect a result of the experiment. This arbitrariness may become an uncertain factor of a result of an experiment. However, when only one pipette is used, processes that can be handled are limited.

A processing system according to an embodiment of the present invention, a control method according to an embodiment of the present invention, an operation command generating device according to an embodiment of the present invention and a computer program according to an embodiment of the present invention allow processes that can be handled to be increased while allowing uncertain factors with respect to an experimental result to be reduced.

A processing system according to one aspect of the present invention includes: a manual pipette that performs suction and discharge of a liquid by moving a piston by an external drive force; an automatic pipette that performs suction and discharge of a liquid by moving a piston by a built-in actuator; at least one robotic arm that selectively grasps the manual pipette or the automatic pipette when suction and discharge of a liquid are performed; and a robotic arm control device that controls at least the robotic arm.

A processing system according to another aspect of the present invention may include: a first robotic arm that selectively grasps the manual pipette or the automatic pipette; and a second robotic arm that moves the piston of the manual pipette that is grasped by the first robotic arm.

In a processing system according to another aspect of the present invention, the robotic arm control device may include: a first controller that performs control in which the first robotic arm is caused to grasp the manual pipette based on a first operation command that is included in an operation command that is a collection of jobs that control the processing system; and a second controller that performs control in which the first robotic arm is caused to grasp the automatic pipette based on a second operation command that is included in the operation command.

A processing system according to another aspect of the present invention may further include an operation command generating device that generates the operation command based on multiple process symbols, which respectively represent processes with respect to a processing target or processes with respect to a container that contains the processing target, and of which processing orders are determined. The operation command generating device may include: a determination part that determines whether to use the manual pipette or the automatic pipette based on the process symbols; a first operation command generation part that generates a first operation command that causes the robotic arm to grasp the manual pipette when the determination part has determined that the manual pipette is used; and a second operation command generation part that generates a second operation command that causes the robotic arm to grasp the automatic pipette when the determination part has determined that the automatic pipette is used.

In a processing system according to another aspect of the present invention, when the process symbols are associated with a specification of a particular mode of suction and discharge, based on the specification of the mode, the determination part may determine whether to use the manual pipette or the automatic pipette.

In a processing system according to another aspect of the present invention, when the specification of the mode is a specification of a speed and the speed changes with time, the determination part may determine that the manual pipette is used, and the first operation command generation part may generate the first operation command that causes the second robotic arm to move the piston at a speed that changes with time corresponding to the above-mentioned speed.

In a processing system according to another aspect of the present invention, when the specification of the mode is a specification of a speed of suction or discharge to which the automatic pipette does not correspond, the determination part may determine that the manual pipette is used, and the first operation command generation part may generate the first operation command that causes the second robotic arm to move the piston at a speed that corresponds to the above-mentioned speed.

In a processing system according to another aspect of the present invention, when the specification of the mode is a specification for discharging a liquid contained in a pipette into multiple containers, the determination part may determine that the automatic pipette is used, and the second operation command generation part may generate the second operation command that causes the first robotic arm to operate and causes a liquid that is sucked into the automatic pipette to be sequentially discharged into the multiple containers.

In a processing system according to another aspect of the present invention, the specification of the mode may be a follow specification for causing the manual pipette or the automatic pipette to move so as to follow a change in a position of a liquid level of a liquid contained in the container.

In a processing system according to another aspect of the present invention, when the specification of the mode is the follow specification, the determination part may determine that the manual pipette is used, and the first operation command generation part may generate the first operation command that causes control of the robotic arm to be performed in which the change in the position of the liquid level of the liquid is predicted.

In a processing system according to another aspect of the present invention, when the specification of the mode is the follow specification and a specification involving photographing the change in the position of the liquid level of the liquid, the determination part may determine that the automatic pipette is used, and the second operation command generation part may generate the second operation command that causes control of the robotic arm to be performed in which the photographed change in the position of the liquid level of the liquid is followed.

In a processing system according to another aspect of the present invention, when the specification of the mode is a specification for sucking a liquid contained in the container or for discharging a liquid into the container by tilting the container and a pipette, the determination part may determine that the automatic pipette is used, and the second operation command generation part may generate the second operation command that causes the second robotic arm to grasp the container, causes the container and the automatic pipette to be tilted, and causes the liquid contained in the container to be sucked or causes a liquid to be discharged into the container.

In a processing system according to another aspect of the present invention, when the process symbols do not include a specification of a particular mode of suction and discharge, based on at least a volume of suction and discharge, the determination part may determine whether to use the manual pipette or the automatic pipette.

A control method of a processing system according to another aspect of the present invention includes: determining whether to use the manual pipette or the automatic pipette based on multiple process symbols, which respectively represent processes with respect to a processing target or processes with respect to a container that contains the processing target, and of which processing orders are determined; generating a first operation command when it is determined that the manual pipette is used; generating a second operation command when it is determined that the automatic pipette is used; causing the robotic arm to grasp the manual pipette based on the first operation command; and causing the robotic arm robotic arm to grasp the automatic pipette based on the second operation command.

An operation command generating device according to another aspect of the present invention generates an operation command based on multiple process symbols, the operation command being a collection of jobs that control a control target that includes at least one robotic arm that performs a process with respect to a processing target, the multiple process symbols respectively representing processes with respect to the processing target or processes with respect to a container that contains the processing target, and processing orders of the multiple process symbols having been determined. The operation command generating device includes: a determination part that determines whether to use a manual pipette or an automatic pipette based on the process symbols, the manual pipette performing suction and discharge of a liquid by moving a piston by an external drive force, and the automatic pipette performing suction and discharge of a liquid by moving a piston by a built-in actuator; a first operation command generation part that generates a first operation command that causes the robotic arm to grasp the manual pipette when the determination part has determined that the manual pipette is used; and a second operation command generation part that generates a second operation command that causes robotic arm to grasp the automatic pipette when the determination part has determined that the automatic pipette is used.

A computer program according to another aspect of the present invention causes a computer to function as the above-described operation command generating device.

Obviously, numerous modifications and variations of the present invention are possible in light of the above teachings. It is therefore to be understood that within the scope of the appended claims, the invention may be practiced otherwise than as specifically described herein.

The invention claimed is:

1. A processing system for processing an experiment of one of biochemistry, biology and biotechnology, comprising:
   a manual pipette comprising a piston and configured to suction and discharge a liquid when the piston of the manual pipette is moved by an external drive force;
   an automatic pipette comprising a piston and a built-in actuator and configured to suction and discharge a liquid when the piston of the automatic pipette is moved by the built-in actuator;
   a robot comprising a first robotic arm configured to select and grasp one of the manual pipette and the automatic pipette based on an operation command and a second robotic arm configured to move the piston of the manual pipette grasped by the first robotic arm; and
   a robotic arm control device comprising circuitry configured to control the robot such that the first robotic arm selects and grasps one of the manual pipette and the automatic pipette based on the operation command,
   the operation command comprising a collection of jobs that controls a plurality of processes for processing at least one of a processing target in an experiment of one of biochemistry, biology and biotechnology and a container containing the processing target in a processing order; and
   an operation command generating device comprising circuitry configured to generate the operation command based on a plurality of process symbols which represents the pluality of processes for at least one of the processing target and the container in the processing order,
   the circuitry of the robotic arm control device comprises first circuitry configured to control the first robotic arm such that the first robotic arm selects and grasps the manual pipette based on a first operation command in the operation command, and second circuitry configured to control the first robotic arm such that the first robotic arm grasps the automatic pipette based on a second operation command in the operation command,
   the circuitry of the operation command generating device is configured to determine which one of the manual pipette and the automatic pipette is to be used based on the process symbols, generate the first operation command when the manual pipette is determined to be used, and generate the second operation command when the automatic pipette is determined to be used,
   the circuitry of the operation command generating device is configured to determine which one of the manual pipette and the automatic pipette is to be used, when a process symbol in the process symbols is associated with a specification of a suction and discharge mode, based on the specification of the suction and discharge mode, and
   the circuitry of the operation command generating device is configured to determine, when the specification of the suction and discharge mode is a specification of a speed which changes with time, that the manual pipette is to be used, and the first circuitry of the robotic arm control device is configured to generate the first operation command that causes the second robotic arm to move the piston of the manual pipette at the speed that changes with time.

2. A processing system according to claim 1, wherein the circuitry of the operation command generating device is configured to determine, when the specification of the suction and discharge mode is a specification of a speed of suction or discharge to which the automatic pipette does not correspond, that the manual pipette is to be used, and the first circuitry of the robotic arm control device is configured to generate the first operation command that causes the second robotic arm to move the piston of the manual pipette at the speed of suction or discharge.

3. A processing system according to claim 1, wherein the circuitry of the operation command generating device is configured to determine, when the specification of the suction and discharge mode is a specification for discharging a liquid contained in a pipette into a plurality of containers, that the automatic pipette is to be used, and the second circuitry of the robotic arm control device is configured to generate the second operation command that causes the first robotic arm to operate and causes the liquid in the automatic pipette to be sequentially discharged into the plurality of containers.

4. A processing system according to claim 1, wherein the specification of the suction and discharge mode is a follow specification for causing the manual pipette or the automatic pipette to move such that the manual pipette or the automatic pipette follows a change in a position of a liquid level of a liquid contained in the container.

5. A processing system according to claim 4, wherein the circuitry of the operation command generating device is configured to determine, when the specification of the suction and discharge mode is the follow specification, that the manual pipette is to be used, and the first circuitry of the robotic arm control device is configured to generate the first operation command that causes the first robotic arm to be controlled such that the first robotic arm predicts the change in the position of the liquid level of the liquid.

6. A processing system according to claim 4, wherein the circuitry of the operation command generating device is configured to determine, when the specification of the suction and discharge mode is the follow specification accompanied by a specification including photographing the change in the position of the liquid level of the liquid, that the automatic pipette is to be used, and the second circuitry of the robotic arm control device is configured to generate the second operation command that causes the robotic arm to be controlled such that the first robotic arm follows a photographed change in the position of the liquid level of the liquid.

7. A processing system according to claim 1, wherein the circuitry of the operation command generating device is configured to determine, when the specification of the suction and discharge mode is a specification for sucking a liquid contained in the container or for discharging a liquid into the container by tilting the container and the manual or automatic pipette, that the automatic pipette is to be used, and the second circuitry of the robotic arm control device is configured to generate the second operation command that causes the second robotic arm to grasp the container, causes the container and the automatic pipette to be tilted, and causes the liquid contained in the container to be sucked or causes the liquid to be discharged from the automatic pipette into the container.

8. A processing system according to claim 1, wherein the circuitry of the operation command generating device is configured to determine, when the process symbols do not include a specification of a suction and discharge mode, which one of the manual pipette and the automatic pipette to be used based on at least a volume of suction and discharge.

9. A processing system according to claim 1, wherein the circuitry of the operation command generating device is configured to determine, when the specification of the suction and discharge mode is a specification of a speed of suction or discharge to which the automatic pipette does not correspond, that the manual pipette is to be used, and the first circuitry of the robotic arm control device is configured to generate the first operation command that causes the second robotic arm to move the piston of the manual pipette at the speed of suction or discharge.

10. A processing system according to claim 1, wherein the circuitry of the operation command generating device is configured to determine, when the specification of the suction and discharge mode is a specification for discharging a liquid contained in a pipette into a plurality of containers, that the automatic pipette is to be used, and the second circuitry of the robotic arm control device is configured to generate the second operation command that causes the first robotic arm to operate and causes the liquid in the automatic pipette to be sequentially discharged into the plurality of containers.

* * * * *